(12) United States Patent
Hockersmith et al.

(10) Patent No.: US 7,440,786 B2
(45) Date of Patent: Oct. 21, 2008

(54) METHOD AND APPARATUS FOR PRESENTATION OF NONINVASIVE GLUCOSE CONCENTRATION INFORMATION

(75) Inventors: Linda J. Hockersmith, Scottsdale, AZ (US); Kevin H. Hazen, Gilbert, AZ (US); Timothy L. Ruchti, Gilbert, AZ (US)

(73) Assignee: Sensys Medical, Inc., Chandler, AZ (US)

( * ) Notice: Subject to any disclaimer, the term of this patent is extended or adjusted under 35 U.S.C. 154(b) by 400 days.

(21) Appl. No.: 11/012,428

(22) Filed: Dec. 14, 2004

(65) Prior Publication Data

US 2005/0209515 A1   Sep. 22, 2005

Related U.S. Application Data

(63) Continuation-in-part of application No. 10/472,856, filed as application No. PCT/US03/07065 on Mar. 7, 2003, now Pat. No. 7,133,710.

(60) Provisional application No. 60/534,829, filed on Jan. 6, 2004, provisional application No. 60/362,885, filed on Mar. 8, 2002.

(51) Int. Cl.
*A61B 5/1455* (2006.01)

(52) U.S. Cl. ..................................... 600/316

(58) Field of Classification Search .................. 600/310, 600/316, 322, 473
See application file for complete search history.

(56) References Cited

U.S. PATENT DOCUMENTS

| | | | | |
|---|---|---|---|---|
| 5,398,681 A | * | 3/1995 | Kupershmidt | 600/316 |
| 5,517,301 A | * | 5/1996 | Dave | 356/237.1 |
| 5,730,140 A | * | 3/1998 | Fitch | 600/514 |
| 5,912,656 A | * | 6/1999 | Tham et al. | 600/300 |
| 6,240,306 B1 | * | 5/2001 | Rohrscheib et al. | 600/316 |
| 6,641,533 B2 | * | 11/2003 | Causey et al. | 600/300 |

* cited by examiner

*Primary Examiner*—Eric F Winakur
(74) *Attorney, Agent, or Firm*—Glenn Patent Group; Michael A. Glenn

(57) ABSTRACT

The invention relates generally to the extraction and/or presentation of glucose concentrations estimated as a function of time into a format that facilitates conveyance of the underlying information. More particularly, glucose concentration histories are presented in terms of risk of behavior, in a video format, and/or in an audio format. The reduction of data into video format, selected by time period, cluster, or glucose concentration response, into an animated or video presentation allows diagnosis and treatment information to be more readily determined and used. Alternatively, glucose concentrations are output through a voice synthesizer or an earcon. These information presentations are useful for both the medical professional and the end user. The information presentation is preferably used with a noninvasive, implantable, semi-continuous, and/or continuous analyte analyzer, such as a glucose concentration analyzer.

25 Claims, 8 Drawing Sheets

METHOD AND APPARATUS FOR PRESENTATION OF NONINVASIVE GLUCOSE CONCENTRATION INFORMATION

CROSS REFERENCE TO RELATED APPLICATION

This application:

claims benefit of U.S. provisional patent application Ser. No. 60/534,829, filed which is herein incorporated in its entirety by this reference thereto. Jan. 6, 2004, and is a continuation-in-part of U.S. patent application Ser. No. 10/472,856, filed Sep. 18, 2003, now U.S. Pat. No. 7,133,710, which is a national stage entry of PCT Application No. PCT/US03/07065, filed Mar. 7, 2003, which claims benefit of U.S. provisional patent application Ser. No. 60/362,885, filed Mar. 8, 2002, each of video format, and/or in an audio format.

BACKGROUND OF THE INVENTION

1. Technical Field

The invention relates generally to the extraction and/or presentation of glucose concentrations estimated as a function of time into a format that facilitates conveyance of the underlying information. More particulauly, glucose concentration histories are presented in terms of risk of behavior, in a video format, and/or in an audio format.

2. Description of the Prior Arts

Diabetes

Diabetes is a chronic disease that results in abnormal production and use of insulin, a hormone that facilitates glucose uptake into cells. While a precise cause of diabetes is unknown, genetic factors, environmental factors, and obesity play roles. Diabetics have increased risk in three broad categories: cardiovascular heart disease, retinopathy, and neuropathy. Diabetics often have one or more of the following complications: heart disease and stroke, high blood pressure, kidney disease, neuropathy, e.g. nerve disease and amputations, retinopathy, diabetic ketoacidosis, skin conditions, gum disease, impotence, and fetal complications. Diabetes is a leading cause of death and disability worldwide. Moreover, diabetes is merely one among a group of disorders of glucose metabolism that also includes impaired glucose tolerance and hyperinsulinemia, which is also known as hypoglycemia.

Diabetes Prevalence and Trends

The prevalence of individuals with diabetes is increasing with time. The World Health Organization (WHO) estimates that diabetes currently afflicts 154 million people worldwide. There are 54 million people with diabetes living in developed countries. The WHO estimates that the number of people with diabetes will grow to 300 million by the year 2025. In the United States, 15.7 million people or 5.9 percent of the population are estimated to have diabetes. Within the United States, the prevalence of adults diagnosed with diabetes increased by 6% in 1999 and rose by 33% between 1990 and 1998. This corresponds to approximately eight hundred thousand new cases every year in America. The estimated total cost to the United States economy alone exceeds $90 billion per year. *Diabetes Statistics*, National Institutes of Health, Publication No. 98-3926, Bethesda, Md. (November 1997).

Long-term clinical studies demonstrate that the onset of diabetes related complications is significantly reduced through proper control of blood glucose concentrations. The Diabetes Control and Complications Trial Research Group, *The effect of intensive treatment of diabetes on the development and progression of long-term complications in insulin-dependent diabetes mellitus*, N. Eng. J. of Med., 329:977-86 (1993); U.K. Prospective Diabetes Study (UKPDS) Group, *Intensive blood-glucose control with sulphonylureas or insulin compared with conventional treatment and risk of complications in patients with type 2 diabetes*, Lancet, 352:837-853 (1998); and Y. Ohkubo, H. Kishikawa, E. Araki, T. Miyata, S. Isami, S. Motoyoshi, Y. Kojima, N. Furuyoshi, M. Shichizi, *Intensive insulin therapy prevents the progression of diabetic microvascular complications in Japanese patients with non-insulin-dependent diabetes mellitus: a randomized prospective 6-year study*, Diabetes Res. Clin. Pract., 28:13-117 (1995).

A vital element of diabetes management is the self-monitoring of blood glucose concentration by diabetics in the home environment. However, current monitoring techniques discourage regular use due to the inconvenient and painful nature of drawing blood or interstitial fluid through the skin prior to analysis, The Diabetes Control and Complication Trial Research Group, supra. Unfortunately, recent reports indicate that even periodic measurement of glucose by individuals with diabetes e.g. seven times per day is insufficient to detect important glucose fluctuations and properly manage the disease. In addition, nocturnal monitoring of glucose concentrations is of significant value but is difficult to perform due to the state of existing technology. Therefore, a device, such as a noninvasive glucose analyzer, that provides noninvasive, automatic, and nearly continuous estimations of glucose concentration is identified as a beneficial development for the management of diabetes. Implantable glucose concentration analyzers coupled to an insulin delivery system providing an artificial pancreas are also being pursued.

Timing

Historically, the extreme majority of traditional glucose concentration determinations have been discrete glucose concentration measurements at irregular or widely spaced time intervals. For example, a subject or user may test their fasting glucose concentration in the morning. Similarly, the user optionally generates a glucose concentration determination before or after a meal or according to a fixed protocol. A number of traditional technologies have been used for these determinations, such as enzymatic, electro-enzymatic, or colorimetric based technologies.

A discrete blood or body chemistry analyte determination is appropriate for the determination of body constituents that do not change rapidly with time. For example, the measurement of plasma albumin does not change rapidly. Other body constituents, such as triglycerides, change more rapidly and hence information is generated based upon their concentration change with time. However, even for these analytes fasting concentrations and/or widely separated concentration determinations are often adequate.

Widely separated in time discrete glucose concentration determinations are less appropriate than a history of well timed glucose concentration determinations. A major problem with widely separated or discrete glucose determinations is that the glucose concentration in the body may change rapidly, especially in diabetics or in pre-diabetics. The degree and/or rate of glucose concentration change is dependent upon a large number of factors including but not limited to the subject's insulin resistance, exercise level, mitigating drug intake, and carbohydrate and food intake history. The transient hyperglycemic and hypoglycemic periods, that are often missed with irregular testing, are of great interest to both the medical professional and tested subject. Recently, a number of analyzers that facilitate a larger number of glucose concentration estimations during a time period have become available that generate semi-continuous or continuous glucose concentrations for a subject. These technologies are an attempt at catching the hyperglycemic and hypoglycemic periods and are reviewed, infra.

Invasive and Minimally Invasive Technologies

A number of continuous and semi-continuous analyzers have recently become available. These glucose concentration analyzers are invasive or minimally invasive in nature.

A first example is an alternative invasive electrochemical-enzymatic sensor. One instance is a Cygnus (Redwood City, Calif.) GLUCOWATCH, which is semi-continuous and minimally invasive. The GLUCOWATCH provides only one reading every twenty minutes, each delayed by at least 10 minutes due to the measurement process. The measurement is made through an alternative invasive electrochemical-enzymatic sensor on a sample of interstitial fluid which is drawn through the skin using iontophoresis. Consequently, the limitations of the device include the potential for significant skin irritation, collection of a biohazard, and a limit of three readings per hour. The GLUCOWATCH presents up to a three day history of glucose concentrations as a function of time.

A second example is a partially implantable glucose concentration analyzer. One instance is the MINIMED (Northridge, Calif.) continuous glucose monitoring system, which is a short-term implantable glucose analyzer. The MINIMED system is capable of providing a glucose concentration profile for up to seventy-two hours. The system records a glucose value every five minutes. The technology behind the MINIMED system relies on a probe being invasively implanted into a subcutaneous region followed by a glucose oxidase based reaction producing hydrogen peroxide, which is oxidized at a platinum electrode to produce an analytical current. Notably, the MINIMED system automatically shifts glucose determinations by ten minutes in order to accommodate for a potential dynamic lag between the blood and interstitial glucose. See T. Gross, B. Bode, D. Einhorn, D. Kayne, J. Reed, N. White, and J. Mastrototaro, *Performance evaluation of the MiniMed continuous glucose monitoring system during patient home use*, Diabetes Technology & Therapeutics, vol. 2, pp. 49-56 (2000). Inherent in these approaches are health risks due to the sensor implantation, infections, patient inconvenience, and measurement delay.

A third example is a continuous monitoring fluorescence based glucose sensor. A. Colvin, Optical-based sensing devices especially for in-situ sensing in humans, U.S. Pat. No. 6,304,766 (Oct. 16, 2001); A. Colvin, G. Daniloff, A. Kalivretenos, D. Parker, E. Ullman, A. Nikolaitchik, Detection of analytes by fluorescent lanthanide metal chelate complexes containing substituted ligands, U.S. Pat. No. 6,334,360 (Feb. 5, 2002); and J. Lesho, Implanted sensor processing system and method for processing implanted sensor output, U.S. Pat. No. 6,400,974 (Jun. 4, 2002) describe an indicator molecule that is combined into an implantable device that is coupled via telemetry to an external device. The device works via an indicator molecule that reversibly binds to glucose. With a light emitting diode for excitation, the indicator molecule fluoresces in the presence of glucose. This device is an example of a short-term implantable with development towards a long-term implantable.

Notably, none of these technologies are noninvasive. Further, none of these technologies offer continuous glucose concentration determination. Finally, none of these technologies use data reduction to represent the glucose concentrations as presented herein.

Noninvasive Technologies

There exist a number of noninvasive approaches for estimation or determination of glucose concentration. These approaches vary widely, but have at least two common steps. First, an apparatus is used to acquire a reading from the body without obtaining a biological sample. Second, an algorithm is used to convert this reading into an estimated glucose concentration.

Noninvasive techniques sample skin, the skin surface, interstitial fluid, tissue, and/or blood. Regions or volumes of the body subjected to noninvasive measurements are: a hand, finger, palmar region, base of thumb, forearm, between the wrist and elbow on the back of the arm, volar aspect of the forearm, dorsal aspect of the forearm, upper arm, head, earlobe, eye, tongue, chest, torso, abdominal region, thigh, calf, foot, plantar region, and toe. It is important to note that noninvasive techniques do not have to be based upon spectroscopy. For example, a bioimpedence meter is a noninvasive device. In this document, any device that reads glucose concentration from the body without penetrating the skin and collecting a biological sample is referred to as a noninvasive glucose concentration analyzer.

One species of noninvasive glucose concentration analyzers are those analyzers based upon the collection and analysis of spectra. Typically, a noninvasive apparatus uses some form of spectroscopy to acquire the signal or spectrum from the body. Spectroscopic techniques used for noninvasive glucose concentration estimation include but are not limited to Raman and fluorescence, as well as techniques using light from the ultraviolet through the infrared [ultraviolet (200 to 400 nm), visible (400 to 700 nm), near-infrared (700 to 2500 nm or 14,286 to 4000 $cm^{-1}$), and infrared (2500 to 14,285 nm or 4000 to 700 $cm^{-1}$)]. These techniques are used with a range of preprocessing approaches, outlier detection, chemometrics, calibration, and prediction techniques for noninvasive, minimally invasive, and implantable devices.

There are a number of reports on noninvasive glucose technologies. Some of these relate to general instrumentation configurations required for noninvasive glucose concentration determination while others refer to sampling technologies. Those related to the present invention are briefly reviewed here:

General Instrumentation

K. Schlager, Non-invasive near infrared measurement of blood analyte concentrations, U.S. Pat. No. 4,882,492, (Nov. 21, 1989) describes a dual beam noninvasive glucose analyzer.

R. Barnes, J. Brasch, D. Purdy, W. Lougheed, Non-invasive determination of analyte concentration in body of mammals, U.S. Pat. No. 5,379,764 (Jan. 10, 1995) describe a noninvasive glucose concentration determination analyzer that uses data pretreatment in conjunction with a multivariate analysis to determine blood glucose concentrations.

P. Rolfe, Investigating substances in a patient's bloodstream, U.K. patent application ser. no. 2,033,575 (Aug. 24, 1979) describes an apparatus for directing light into the body, detecting attenuated backscattered light, and utilizing the collected signal to determine glucose concentrations in or near the bloodstream.

C. Dahne, D. Gross, Spectrophotometric method and apparatus for the non-invasive, U.S. Pat. No. 4,655,225 (Apr. 7, 1987) describe a method and apparatus for directing light into a patient's body, collecting transmitted or backscattered light, and determining glucose concentrations from selected near-infrared wavelength bands. Wavelengths include 1560 to 1590, 1750 to 1780, 2085 to 2115, and 2255 to 2285 nm with at least one additional reference signal from 1000 to 2700 nm.

A particular range for noninvasive glucose concentration estimation in diffuse reflectance mode is about 1100 to 2500 nm or ranges therein, see K. Hazen, *Glucose determination in biological matrices using near-infrared spectroscopy*, doctoral dissertation, University of Iowa, (1995).

M. Robinson, K. Ward, R. Eaton, D. Haaland, Method and apparatus for determining the similarity of a biological analyte from a model constructed from known biological fluids, U.S. Pat. No. 4,975,581 (Dec. 4, 1990) describe a method and apparatus for measuring a concentration of a biological analyte such as glucose using infrared spectroscopy in conjunction with a multivariate model. The multivariate model is constructed from a plurality of known biological fluid samples.

J. Hall, T. Cadell, Method and device for measuring concentration levels of blood constituents non-invasively, U.S. Pat. No. 5,361,758 (Nov. 8, 1994) describe a noninvasive device and method for determining analyte concentrations within a living subject, using polychromatic light, a wavelength separation device, and an array detector. The apparatus uses a receptor shaped to accept a fingertip with means for blocking extraneous light.

S. Malin, G Khalil, Method and apparatus for multi-spectral analysis of organic blood analytes in noninvasive infrared spectroscopy, U.S. Pat. No. 6,040,578 (Mar. 21, 2000) describe a method and apparatus for determination of an organic blood analyte using multi-spectral analysis in the near-infrared. A plurality of distinct nonoverlapping regions of wavelengths are incident upon a sample surface, diffusely reflected radiation is collected, and the analyte concentration is determined via chemometric techniques.

J. Garside, S. Monfre, B. Elliott, T. Ruchti, G. Kees, Fiber optic illumination and detection patterns, shapes, and locations for use in spectroscopic analysis, U.S. Pat. No. 6,411,373, (Jun. 25, 2002) describe the use of fiber optics for use as excitation and/or collection optics with various spatial distributions.

Specular Reflectance

R. Messerschmidt, D. Sting Blocker device for eliminating specular reflectance from a diffuse reflectance spectrum, U.S. Pat. No. 4,661,706 (Apr. 28, 1987) describe a reduction of specular reflectance by a mechanical device. A blade-like device skims the specular light before it impinges on the detector. A disadvantage of this system is that it does not efficiently collect diffusely reflected light and the alignment is problematic.

R. Messerschmidt, M. Robinson, Diffuse reflectance monitoring apparatus, U.S. Pat. No. 5,636,633 (Jun. 10, 1997) describe a specular control device for diffuse reflectance spectroscopy using a group of reflecting and open sections.

R. Messerschmidt, M. Robinson, Diffuse reflectance monitoring apparatus, U.S. Pat. No. 5,935,062 (Aug. 10, 1999) and R. Messerschmidt, M. Robinson, Diffuse reflectance monitoring apparatus, U.S. Pat. No. 6,230,034 (May 8, 2001) describe a diffuse reflectance control device that discriminates between diffusely reflected light that is reflected from selected depths. This control device additionally acts as a blocker to prevent specularly reflected light from reaching the detector.

Malin, supra describes the use of specularly reflected light in regions of high water absorbance such as 1450 and 1900 nm to mark the presence of outlier spectra wherein the specularly reflected light is not sufficiently reduced.

K. Hazen, G. Acosta, A. Abul-Haj, R. Abul-Haj, Apparatus and method for reproducibly modifying localized absorption and scattering coefficients at a tissue measurement site during optical sampling, U.S. Pat. No. 6,534,012 (Mar. 18, 2003) describe a mechanical device for applying sufficient and reproducible contact of the apparatus to the sampling medium to minimize specular reflectance. Further, the apparatus allows for reproducible applied pressure to the sampling site and reproducible temperature at the sampling site.

Sample Preparation

B. Wenzel, S. Monfre, T. Ruchti, K. Meissner, F. Grochocki, T. Blank, J. Rennert, A method for quantification of stratum corneum hydration using diffuse reflectance spectroscopy, U.S. Pat. No. 6,442,408, (Aug. 27, 2002) describe a method and apparatus for determination of tissue variability, such as water content of the epidermal ridge and penetration depth of incident light.

Temperature

K. Hazen, *Glucose Determination in Biological Matrices Using Near-Infrared Spectroscopy*, doctoral dissertation, University of Iowa (1995) describes the adverse effect of temperature on near-infrared based glucose concentration determinations. Physiological constituents have near-infrared absorbance spectra that are sensitive, in terms of magnitude and location, to localized temperature and the sensitivity impacts noninvasive glucose concentration determination.

Coupling Fluid

A number of sources describe coupling fluids with important sampling parameters.

Index of refraction matching between the sampling apparatus and sampled medium is well known. Glycerol is a common index matching fluid for optics to skin.

R. Messerschmidt, Method for non-invasive blood analyte measurement with improved optical interface, U.S. Pat. No. 5,655,530 (Aug. 12, 1997), and R. Messerschmidt, Method for non-invasive blood analyte measurement with improved optical interface, U.S. Pat. No. 5,823,951 describe an index-matching medium for use between a sensor probe and the skin surface. The index-matching medium is a composition containing perfluorocarbons and chlorofluorocarbons.

M. Robinson, R. Messerschmidt, Method for non-invasive blood analyte measurement with improved optical interface, U.S. Pat. No. 6,152,876 (Nov. 28, 2000) and M. Rohrscheib, C. Gardner, M. Robinson, Method and apparatus for non-invasive blood analyte measurement with fluid compartment equilibration, U.S. Pat. No. 6,240,36 (May 29, 2001) describe an index-matching medium to improve the interface between the sensor probe and skin surface during spectroscopic analysis. The index-matching medium is preferably a composition containing chlorofluorocarbons with optional perfluorocarbons.

T. Blank, G. Acosta, M. Mattu, S. Monfre, Fiber optic probe guide placement guide, U.S. Pat. No. 6,415,167 (Jul. 2, 2002) describe a coupling fluid of one or more perfluoro compounds where a quantity of the coupling fluid is placed at an interface of the optical probe and measurement site. Perfluoro compounds do not have the toxicity associated with chlorofluorocarbons.

Positioning

T. Blank, supra describes the use of a guide in conjunction with a noninvasive glucose concentration analyzer in order to increase precision of the location of the sampled tissue site resulting in increased accuracy and precision in noninvasive glucose concentration estimations.

J. Griffith, P. Cooper, T. Barker, Method and apparatus for non-invasive blood glucose sensing, U.S. Pat. No. 6,088,605 (Jul. 11, 2000) describe an analyzer with a patient forearm interface in which the forearm of the patient is moved in an incremental manner along the longitudinal axis of the patient's forearm. Spectra collected at incremental distances are averaged to take into account variations in the biological components of the skin. Between measurements rollers are used to raise the arm, move the arm relative to the apparatus and lower the arm by disengaging a solenoid causing the skin lifting mechanism to lower the arm into a new contact with the sensor head.

Pressure

E. Chan, B. Sorg, D. Protsenko, M. O'Neil, M. Motamedi, A. Welch, *Effects of compression on soft tissue optical properties*, IEEE Journal of Selected Topics in Quantum Electronics, Vol. 2, no. 4, pp. 943-950 (1996) describe the effect of pressure on absorption and reduced scattering coefficients from 400 to 1800 nm. Most specimens show an increase in the scattering coefficient with compression.

K. Hazen, G. Acosta, A. Abul-Haj, R. Abul-Haj, Apparatus and method for reproducibly modifying localized absorption and scattering coefficients at a tissue measurement site during optical sampling, U.S. Pat. No. 6,534,012 (Mar. 18, 2003) describe in a first embodiment a noninvasive glucose concentration estimation apparatus for either varying the pressure applied to a sample site or maintaining a constant pressure on a sample site in a controlled and reproducible manner by moving a sample probe along the z-axis perpendicular to the sample site surface. In an additional described embodiment, the arm sample site platform is moved along the z-axis that is perpendicular to the plane defined by the sample surface by raising or lowering the sample holder platform relative to the analyzer probe tip. The '012 patent further teaches proper contact to be the moment specularly reflected light is about zero at the water bands at 1950 and 2500 nm.

M. Makarewicz, M. Mattu, T. Blank, G. Acosta, E. Handy, W. Hay, T. Stippick, B. Richie, Method and apparatus for minimizing spectral interference due to within and between sample variations during in-situ spectral sampling of tissue, U.S. patent application Ser. No. 09/954,856 (filed Sep. 17, 2001) describe a temperature and pressure controlled sample interface. The means of pressure control are a set of supports for the sample that control the natural position of the sample probe relative to the sample.

Data Processing

R. Barnes, J. Brasch, Non-invasive determination of glucose concentration in body of patients, U.S. Pat. No. 5,070, 874, (Dec. 10, 1991) describe a method of collecting near-infrared noninvasive spectra, preprocessing with an $n^{th}$ derivative, and determining a glucose concentration from the resulting spectrum.

Several approaches exist that employ diverse preprocessing methods to remove spectral variation related to the sample and instrumental variation including normalization, smoothing, derivatives, multiplicative signal correction, [P. Geladi, D. McDougall, H. Martens, *Linearization and scatter-correction for near-infrared reflectance spectra of meat*, Applied Spectroscopy, vol. 39, 491-500, (1985)], standard normal variate transformation, [R. Barnes, M. Dhanoa, S. Lister, *Applied Spectroscopy*, 43, 772-777, (1989)], piecewise multiplicative scatter correction, [T. Isaksson and B. Kowalski, *Applied Spectroscopy*, 47, 702-709, (1993)], extended multiplicative signal correction, [H. Martens, E. Stark, *J. Pharm Biomed Anal*, 9, 625-635, (1991)], pathlength correction with chemical modeling and optimized scaling, [*GlucoWatch automatic glucose biographer and autosensors*, Cygnus Inc., Document #1992-00, Rev. March (2001)], and finite impulse response filtering, [S. Sum, *Spectral signal correction for multivariate calibration*, Doctoral Dissertation, University of Delaware, (1998); S. Sum, and S. Brown, *Standardization of fiber-optic probes for near-infrared multivariate Calibrations*, Applied Spectroscopy, Vol. 52, No. 6, 869-877, (1998); and T. Blank, S. Sum, S. Brown, S. Monfre, *Transfer of near-infrared multivariate calibrations without standards*, Analytical Chemistry, 68, 2987-2995, (1996)].

In addition, a diversity of signal, data or pre-processing techniques are commonly reported with the fundamental goal of enhancing accessibility of the net analyte signal [D. Massart, B. Vandeginste, S. Deming, Y. Michotte, L. Kaufman, *Chemometrics: a textbook*, New York, Elsevier Science Publishing Company, Inc., 215-252, (1990); A. Oppenheim, R. Schafer, *Digital Signal Processing*, Englewood Cliffs, N.J.: Prentice Hall, 1975, 195-271; M. Otto, *Chemometrics*, Weinheim: Wiley-VCH, 51-78, (1999); K. Beebe, R. Pell, M. Seasholtz, *Chemometrics A Practical Guide*, New York: John Wiley & Sons, Inc., 26-55, (1998); M. Sharaf, D. Illman and B. Kowalski, *Chemometrics*, New York: John Wiley & Sons, Inc., 86-112, (1996); and A. Savitzky, M. Golay, *Smoothing and differentiation of data by simplified least squares procedures*, Anal. Chem., vol. 36, no. 8, 1627-1639, (1964)]. A goal of these techniques is to attenuate the noise and instrument variation while maximizing the signal of interest.

Existing Glucose Data Management

Typically, an invasive, minimally invasive, noninvasive, or implantable glucose concentration analyzer presents discrete glucose concentrations. For example, a glucose concentration determination is performed before breakfast, before lunch, and before supper resulting in three glucose concentrations. Some users act upon each discrete glucose concentration without the benefit of seeing long or medium term data. Some users use meters that automatically record a limited history of the glucose concentrations into memory or they manually record some or all of the numbers into a notebook. The user or medical care specialist looks at these numbers and tries to adjust diagnosis or treatment with the data. A meter that records glucose information may record data fields that consist of date, time, and glucose concentration. Other meters may record user identification in addition to the above fields.

Representative glucose concentration data with associated time and user elements are presented in Table 1. A problem with this typical presentation of data in Table format is that underlying information is not readily apparent. For example, the data in Table 1 represents glucose concentrations collected in less than one week. A doctor often has only a minute to exam the data and to decide on an adjustment to the patient's diabetes management protocol. Deciding a treatment based upon the data as presented in Table 1 is difficult. A medical professional may only have time to see highs or lows in the glucose concentration. This problem becomes considerably more complex as the number of glucose concentrations determined in a day increases and/or as the total number of days recorded increases.

TABLE 1

Typical Glucose Concentration Data

| Subject i.d. | Day | Time | a.m./p.m. | Glucose Concentration (mg/dL) |
|---|---|---|---|---|
| 1 | 1 | 7:27 | a.m. | 120 |
| 1 | 1 | 11:33 | a.m. | 188 |
| 2 | 1 | 12:16 | p.m. | 267 |
| 1 | 1 | 6:27 | p.m. | 196 |
| 1 | 2 | 7:33 | a.m. | 115 |
| 1 | 2 | 8:15 | a.m. | 117 |
| 1 | 2 | 11:32 | a.m. | 215 |
| 1 | 2 | 6:30 | p.m. | 232 |
| 2 | 2 | 7:19 | p.m. | 178 |
| 1 | 3 | 7:25 | a.m. | 126 |
| 1 | 3 | 11:50 | a.m. | 196 |
| 3 | 3 | 3:12 | p.m. | 92 |
| 1 | 3 | 7:14 | p.m. | 168 |
| 1 | 3 | 8:14 | a.m. | 133 |

TABLE 1-continued

Typical Glucose Concentration Data

| Subject i.d. | Day | Time | a.m./p.m. | Glucose Concentration (mg/dL) |
|---|---|---|---|---|
| 1 | 4 | 12:02 | p.m. | 175 |
| 2 | 4 | 2:15 | p.m. | 312 |
| 1 | 4 | 6:46 | p.m. | 219 |
| 1 | 4 | 7:18 | a.m. | 115 |
| 1 | 5 | 11:54 | a.m. | 189 |
| 3 | 5 | 4:49 | p.m. | 88 |
| 1 | 5 | 6:46 | p.m. | 248 |
| 1 | 6 | 7:12 | a.m. | 97 |

Some devices present the glucose concentration determined as a function of time. Many devices, such as a fingerstick meter, do not commonly distinguish between users. Hence, the tabulated glucose concentrations as a function of time may represent many users of the device. Even a more advanced device that keeps track of user identification or of a tracking number may have difficulties in presenting the underlying information in the data. For example, the glucose concentrations for only subject number 1 of the Table 1 data is presented in FIG. 1. Again, the underlying patterns of glucose control, or lack of control, are not readily apparent as presented.

A large number of minimally invasive, noninvasive glucose, semi-continuous, and continuous analyzers have recently become available or have been presented in the literature. Many of these analyzers are capable of generating large numbers of glucose concentration readings. Currently, methods of reducing large amounts of glucose data into more manageable information are not used in conjunction with noninvasive glucose meters, semi-continuous, or continuous glucose analyzers. Clearly, as technologies allow for more frequent glucose concentration determinations data management techniques that allow the extraction and presentation of diabetes information from the underlying data becomes increasingly important.

While a number of instruments and data processing approaches exist as described, supra, none of these reports describe methods of reducing the voluminous data into information that is readily absorbed by a professional or lay user in a short period of time.

SUMMARY OF THE INVENTION

The invention involves the extraction and/or presentation of glucose concentrations collected as a function of time into a format that more readily conveys the underlying information. The reduction of data into information allows diagnosis and treatment information to be more readily determined and used. The information presentation is useful for both the medical professional and the end user. The information presentation is preferably used with a noninvasive, implantable, semi-continuous, and/or continuous analyte analyzer, such as a glucose concentration analyzer.

DETAILED DESCRIPTION OF A PREFERRED EMBODIMENT

The following detailed description should be read with reference to the drawings in which similar elements in different drawings are numbered the same. The drawings, which are not necessarily to scale, depict illustrative embodiments that are not intended to limit the scope of the invention.

A noninvasive glucose analyzer is used to describe and teach various embodiments of the invention. Similar methods and apparatus used in conjunction with invasive, semi-invasive, noninvasive, and/or implantable glucose analyzers are also usable with the inventions described herein. In addition, the invention comprises systems that perform and report discrete, semi-continuous, and/or continuous glucose determinations. Further, while this invention is taught using noninvasive glucose determination examples, it is recognized that similar data handling and presentation is optionally used for the presentation of additional analytes that are noninvasively determined, such as urea, cholesterol and its sub-types, pH, oxygen, and other blood or tissue constituents.

Glucose Concentration Analyzer

In a first embodiment of the invention, information is extracted from glucose concentration data and the information is presented in a more manageable format. Details of particular embodiments of the invention are described, infra.

Figure 1:
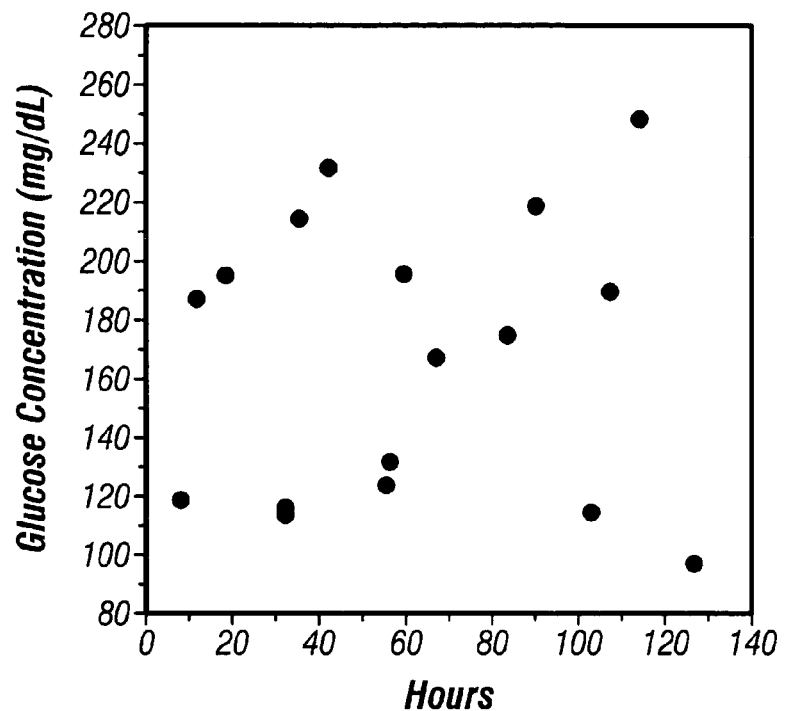
FIG. 1 presents a glucose history of a subject.
Figure 2:
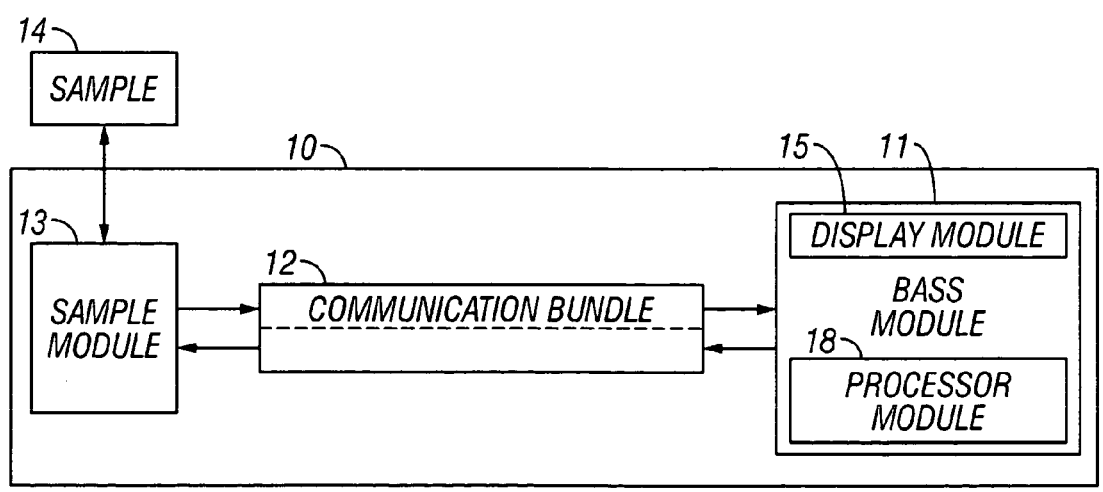
FIG. 2 provides a block drawing of an analyzer according to the invention.

In many embodiments of the invention, an analyzer or a glucose tracking system is used. Referring now to FIG. 2, a block diagram of an analyzer 10 including a split base module 11 and sample module 13 connected via a communication bundle 12 is presented. The analyzer preferably has a display module 15 integrated into the analyzer 10 or base module 11. The system uses a glucose concentration analyzer that comprises at least a source, a sample interface, at least one detector, and an associated algorithm.

Conventionally, all of the components of a noninvasive glucose analyzer are included in a single unit. Herein, the combined base module 11, communication bundle 12, sample module 13, and optional processor module 18 are referred to as a spectrometer and/or analyzer 10. Preferably, the analyzer 10 is physically separated into elements including a base module 11, a communication bundle 12, and a sample module 13. Advantages of separate units include heat, size, and weight management. For example, a separated base module allows for support of the bulk of the analyzer on a stable surface, such as a tabletop or floor. This allows a smaller sample module to interface with a sample, such as human skin tissue. This separation allows a more flexible and/or lighter sample module for use in sampling by an individual. In addition, separate housing requirements are achievable for the base module and sample module in terms of power, weight, and thermal management. In addition, a split analyzer results in less of a physical impact, in terms of mass and/or tissue displacement, on the sample site by the sample module. The sample module, base module, communication bundle, display module, and processor module are further described, infra.

Sample Module

A sample module 13, also referred to as a sampling module, interfaces with a tissue sample and, at the same or different times, with one or more reference materials. The sample module includes a sensor head assembly that provides an interface between the glucose concentration tracking system and the patient. The tip of the sample probe of the sample module is brought into contact with the tissue sample. Optionally, the tip of the sample probe is interfaced to a guide, such as an arm-mounted guide, to conduct data collection and removed when the process is complete. An optional guide accessory includes an occlusion plug that is used to fill the guide cavity when the sensor head is not inserted in the guide, and/or to provide photo-stimulation for circulation enhancement. In one example, the following components are included in the sample module sensor head assembly: a light source, a single fiber optic, and coupling fluid. Preferably, the sample module is in a separate housing from the base module. Alternatively, the sample module is integrated into a single unit with the base module, such as in a handheld or desktop analyzer.

Communication Bundle

A communication bundle 12 is a multi-purpose bundle. The multi-purpose bundle is a flexible sheath that includes at least one of:
 Electrical wires to supply operating power to the lamp in the light source;
 Thermistor wires;
 One or more fiber-optics, which direct diffusely reflected near-infrared light to the spectrograph;
 A tube, used to transport optical coupling fluid from the base unit, through the sensor head, and onto the measurement site;
 A tension member to remove loads on the wiring and fiber-optic strand from pulls; and
 Photo sensor wires.

Further, in the case of a split analyzer the communication bundle allows separation of the mass of the base module from the sample module as described herein. Preferably, the bundle has labeling instructions that teach the user to not twist the bundle and, optionally, mechanical means to prevent it from twisting more than one-quarter turn in either direction. In another embodiment, the communication bundle is in the form of wireless communication. In this embodiment, the communication bundle includes a transmitter, transceiver, and/or a receiver that are mounted into the base module and/or sample module.

Base Module

A portion of the diffusely reflected light from the site is collected and transferred via at least one fiber-optic, free space optics, or an optical pathway to the spectrograph. The spectrograph separates the spectral components of the diffusely reflected light, which are then directed to the photo-diode array (PDA). The PDA converts the sampled light into a corresponding analog electrical signal, which is then conditioned by the analog front-end circuitry. The analog electrical signals are converted into their digital equivalents by the analog circuitry. Digital data are then sent to the digital circuitry where they data are checked for validity, processed, and stored in non-volatile memory. Optionally, the processed results are recalled when the session is complete and after additional processing the individual glucose concentrations are available for display or transfer to a personal computer. The base module also, preferably, includes a processor module, which comprises any of a central processing unit, memory and storage unit, or equivalent for storage of data and/or routines, such as one or more calibration models or net analyte signals. Preferably the base module comprises a display module.

EXAMPLE I

In a first example, an analyzer 10 contained in a single unit, the base module 11, communication bundle 12, and sample module 13 are all integrated together and are contained within or integrated onto a single containing unit.

EXAMPLE II

In a second example, a base module 11 is separated from the sample module 13. Communication exists between the sample module 13 and base module 11 via a communication bundle 12. In varying embodiments, the communication bundle is wireless, carries electrical power, carries data, transmits energy or movement, and/or carries fluid. For example the communication bundle 12 carries feedback control signals, temperature sensing data, coupling fluid, light, data, and/or contains hydraulic fluid.

EXAMPLE III

Figure 3:
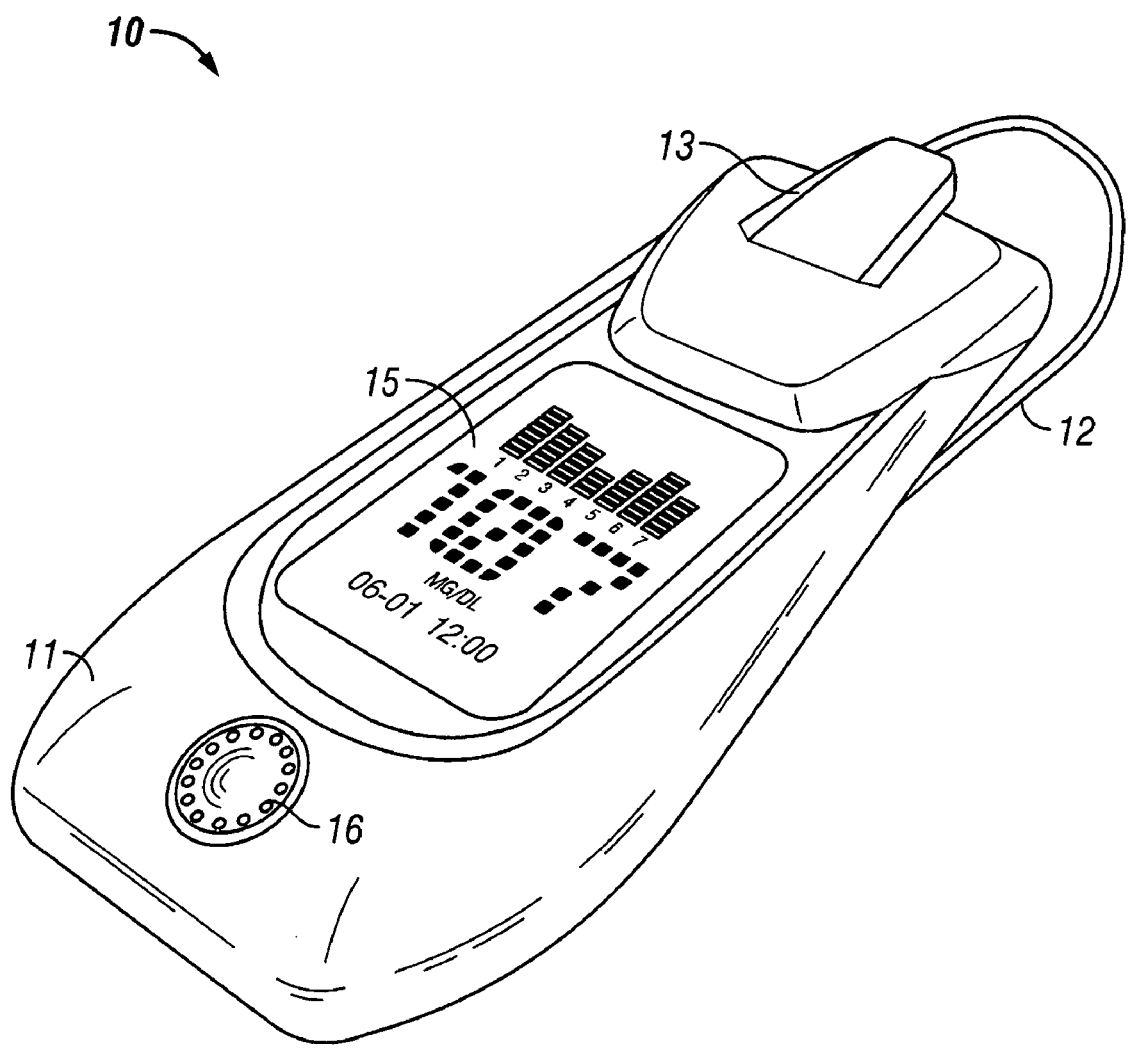
FIG. 3 provides a perspective drawing of a handheld noninvasive glucose analyzer according to the invention.

Referring now to FIG. 3, an example of a handheld analyzer 10 is presented. In this case the base module 11 is separated from the sample module 13 by a communication bundle 12. The sample module 13 docks into the base module when not in use or, optionally, for scanning an internal reference material 14. A graphical display module 15 is integrated into the base module 11. In the example presented, an optional audio output 16 speaker is presented.

EXAMPLE IV

Figure 4:
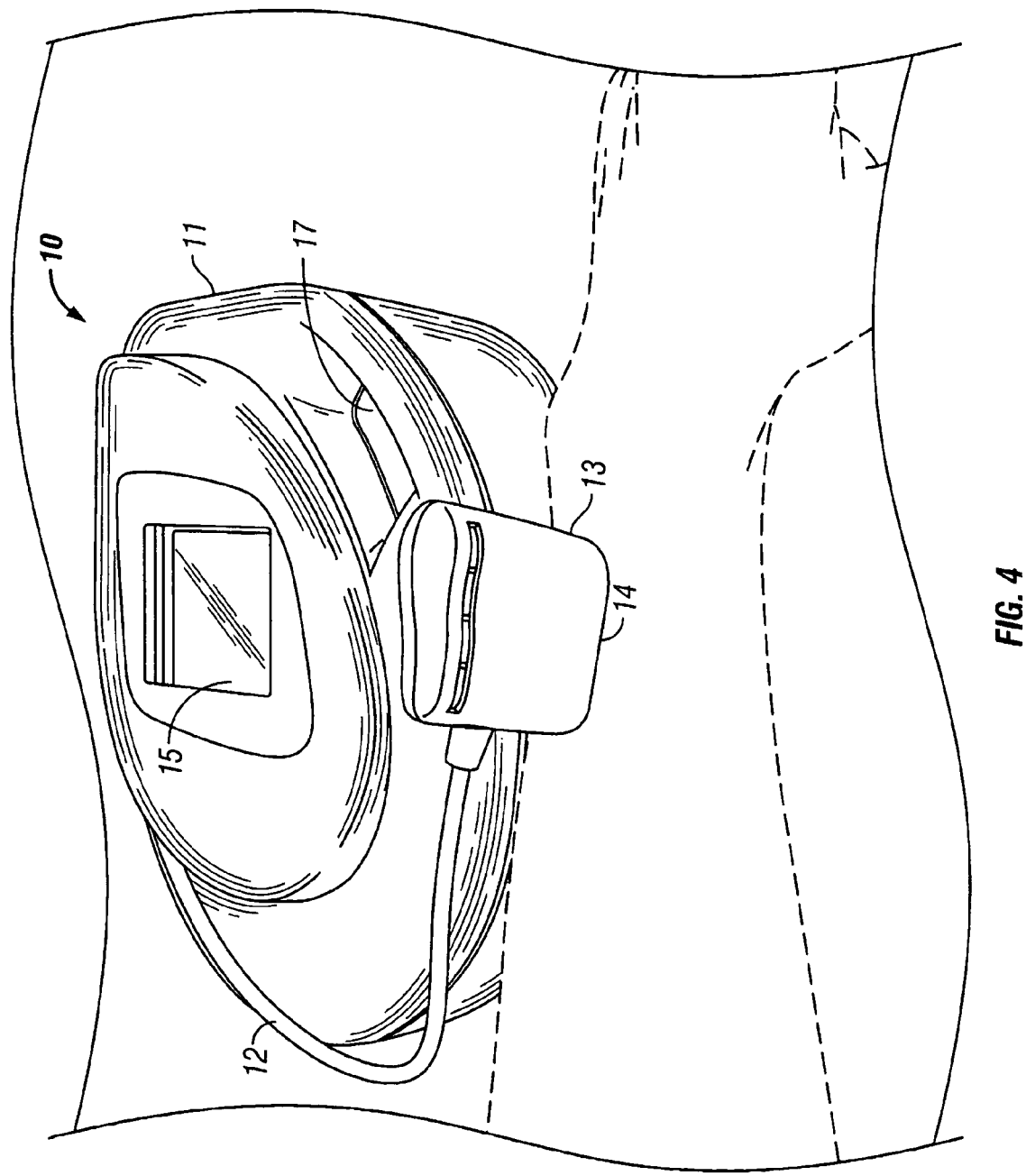
FIG. 4 provides a perspective drawing of a tabletop noninvasive glucose analyzer according to the invention.

Referring now to FIG. 4, an example of a tabletop analyzer is presented. This example presents an analyzer 10 with a base module 11 connected to a sample module 13 via a communication bundle 12. The tip of the sample module 13 is interfaced to a tissue sample 14. In this case, the tissue sample is the dorsal aspect of the forearm between a subject's wrist and elbow. A display module 15 is integrated into the base module 11 and is tilted for easy viewing. Herein, the combined base module 11, communication bundle 12, sample module 13, and display module 15 is referred to as a spectrometer and/or analyzer 10. In this example, an optional docking station 17 is presented where the sample probe 13 is optionally stored when not in use.

Further examples of noninvasive glucose analyzers have been previously presented in U.S. patent application Ser. No. 10/472,856 and U.S. patent application Ser. No. 10/971,447, which are incorporated herein in their entirety by this reference thereto. Of particular importance to this invention are the processor means, memory system, display screen, user inputs, and/or user controls.

Processor Module

An optional processor module 18 converts the detected signal into an analyte concentration estimation and, optionally, controls output of the concentration to the user. Other embodiments of the processor module comprises a processor, processing element, microprocessor, microcontroller, programmable logic circuit, and other types of processing elements known to those skilled in the art.

Display Module

A noninvasive glucose analyzer preferably contains a display module 15 that provides information to the end user or professional. Preferably, the display module 15 is integrated into the base module 11. Optionally, the display module is integrated into the sample module 13 or analyzer 10. The display screen communicates current and/or historical analyte concentrations to a user and/or medical professional in a format that facilitates information uptake from underlying data. A particular example of a display module is a 3.5" ¼ VGA 320×240 pixel screen. The display screen is optionally a color screen, a touch screen, a backlit screen, or is a light emitting diode backlit screen.

A preferable noninvasive glucose analyzer uses a central processing unit (CPU) or equivalent that has an internal or associated memory system. The memory system is capable of maintaining historical estimated glucose concentrations. Optionally, values or entries that are associated with individual glucose concentrations and are stored in memory include subject specific parameters, times, and events. Subject specific parameters include identifiers, such as their name, age, sex, weight, height, and diabetes state history. Preferably, times are recorded for each glucose estimation or event. Examples of events include exercise durations, exercise intensity, hypoglycemic symptoms, a meal, a meal type, the components of a meal, or the make-up of individual or complete meals in terms of any of sugars, fats, proteins, or calories. In its broadest terms, any analyzer determined parameter or user input parameter affecting diabetes management and their associated times is optionally recorded. The CPU allows for transformation of data in memory into information, as described herein. These data are correlated with glucose concentrations and are optionally extracted and presented as being causal or a resultant of food intake, such as a meal, exercise, or diabetes drug treatment intake.

The display screens of glucose analyzers are becoming increasingly powerful. For example, the display 15 in FIG. 3 is preferably capable of graphical and/or video presentations. The optional audio output unit 16, such as a speaker, is capable of emitting tones, tunes, complex sounds, or voice synthesis. These presentation capabilities combined with the digital memories allow for increasingly sophisticated presentation of data. For example, a display screen optionally presents a graphical representation of the user's glucose concentration history as a function of time, as a function of event, or both. Multiple species of presentation are described herein. However, in its broadest sense the display screen allows for static graphical presentations, moving video or slide screen presentations, and/or sound.

User inputs and/or user controls of glucose analyzers are also becoming increasingly powerful. The glucose concentration analyzer presented in FIG. 4 has a display module 15 that is optionally a touch screen. Input is optionally performed with a menu driven button interface or through audio or voice recognition technology. For example, the user may wish to select from or scroll through a series of graphical and/or audio presentation options. These options are optionally customized by the user or for the user.

Information Presentation

Information is generated from data and presented to the user by a number of means and in a number of formats. Some illustrative examples follow.

Function of Time

Time is required for a person to assimilate tabulated glucose concentration data, such as the data presented in Table 1. This type of tabulated data is the typical format for glucose concentration history presentation. Alternative, better methods of presentation of tabulated data are presented, infra.

As a first example, glucose concentrations for an individual are presented graphically as a function of the time, such as a few hours, time associated with an event, a period of less that four hours, a day, a week, or a month.

Figure 5:
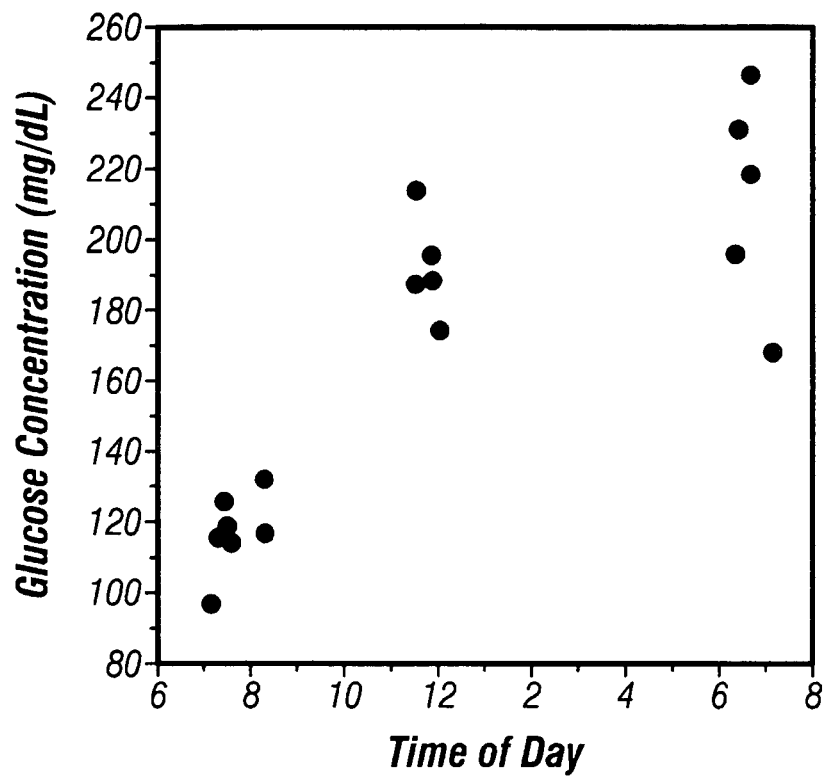
FIG. 5 presents a transformed glucose history according to the invention.

Referring now to FIG. 5, data from subject number one from Table 1 are presented as a function of the time of day. The subject and/or medical professional is presented with the same information in a clearer format. The presentation makes it clear that the subject or patient generally tests their sugar concentration three times a day, that they have acceptable, though slightly high, glucose concentrations in the morning that have tight precision, they have elevated glucose concentrations at or about noon that again have good precision, and they have slightly higher glucose concentrations in the evening with somewhat less precision.

The professional or subject may then query in a targeted fashion. For example, are the patients noon and dinnertime glucose concentrations collected before or after eating? The professional or user may then address habits, such as what they eat for lunch or supper, to establish a plan to reduce their subsequent glucose concentrations. This plot also makes it apparent from the total number of data points in each cluster that the individual test slightly more frequently in the morning.

Also apparent from FIG. 5 is information resulting from areas in the figure without data. For example, no glucose concentrations are observed above 260 mg/dL, and the subject does not test between normal meal times or at night. Presentation in this format helps the subject and/or medical professional to extract information from the tabulated glucose concentration history.

Figure 6:
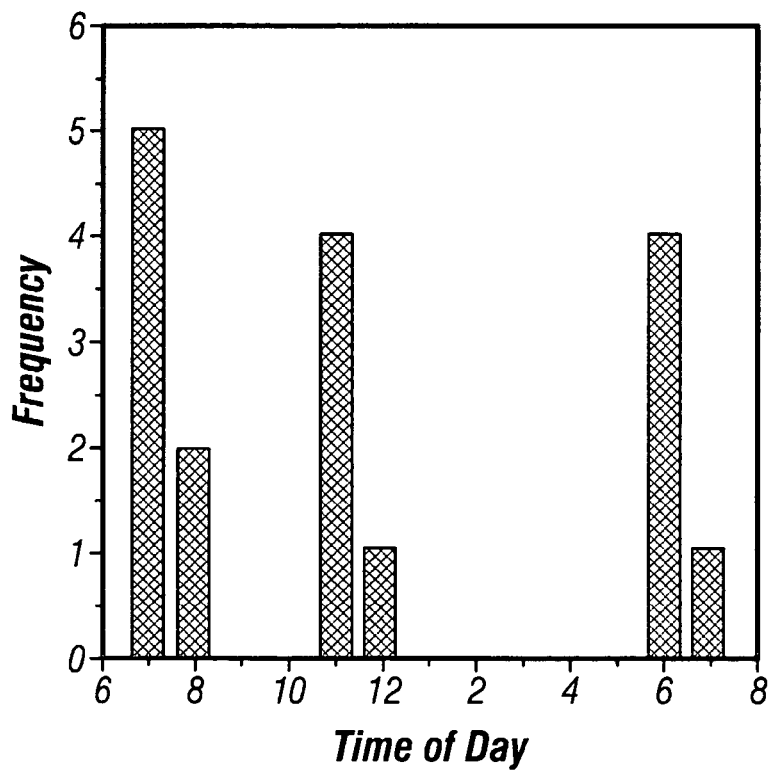
FIG. 6 presents a histogram of glucose testing according to the invention.

A second example also transforms the glucose concentration data as a function of time. Referring now to FIG. 6, data from subject number one from Table 1 are presented as a histogram. FIG. 6 shows the information related to testing habits in a way that they are readily observed. In this case, the subject is observed to test regularly with each meal. In addition, it is observed that the subject does not test between meals or at night.

Figure 7:
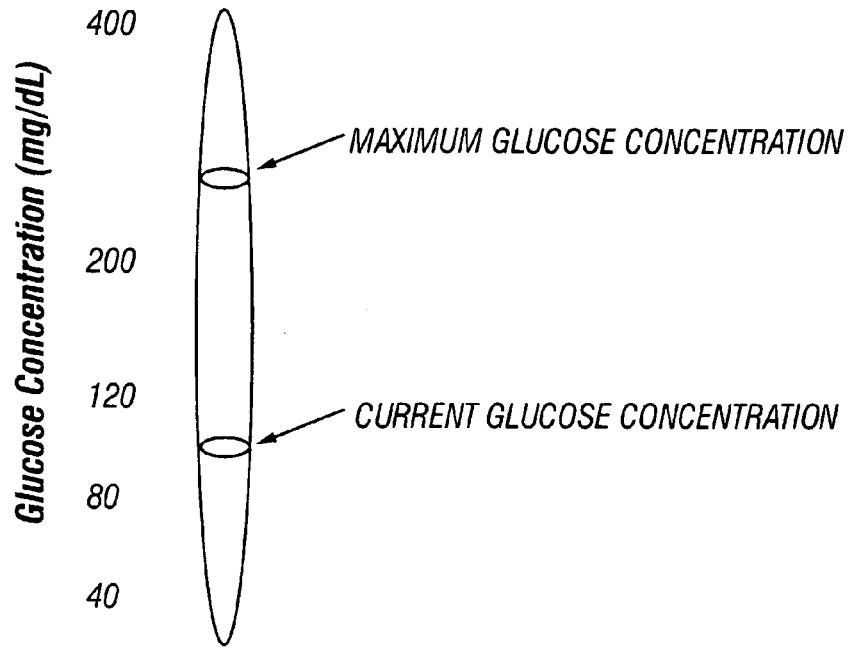
FIG. 7 presents a slide-bar representation of glucose concentrations according to the invention.

A third example uses a graphical representation of current or past glucose concentrations on a slide bar. The slide bar is a graphical representation of a glucose concentration that moves along at least one dimension, as shown in FIG. 7. The slide bar is represented graphically in any orientation. The scale is linear or nonlinear. Different regions of the scale are optionally color coded. For example, the high glucose concentration region or slide bar is in red, the medium in yellow, and the low in blue. Any of a number of regions and corresponding colors are optionally used. More than one slider on the bar is optionally used. For instance, one slider optionally the most recent glucose concentration, while an additional slider represents a local maximum glucose concentration or the highest glucose concentration of a given time period, such as the last number of hours or days. Still another slider optionally illustrates a goal glucose concentration. Additional sliders represent statistical glucose distributions, such as a maximum, minimum, inter-quartile range, sliding average, standard deviation, or other statistics that represent target, historical, current, or projected glucose concentration.

Figure 8:
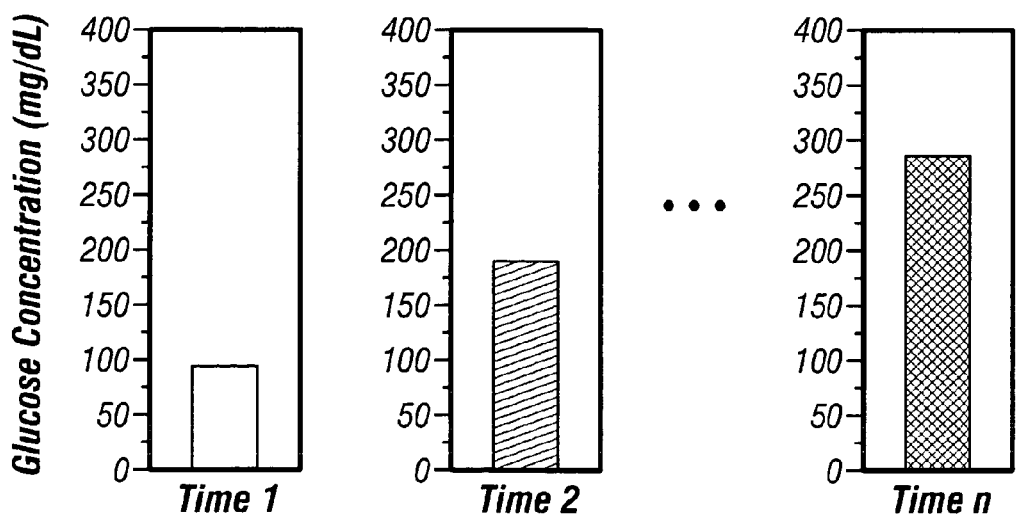
FIG. 8 presents an updateable or replayable bar graph presentation of glucose or transformed glucose concentrations according to the invention.

A fourth example uses a bar graph to represent the glucose concentration. This bar graph is similar to a slide bar. For example, multiple bars represent parameters that are presented in the sliding bar graph, such as historical, current, or statistical presentations of the glucose concentrations. The bar graph is static for a given glucose value. The single bar graph is optionally updated with time, as shown in FIG. 8. The overlapping of the updated data on top of the prior data allows for presentation in a smaller space, with fewer graphic capabilities, and/or with less computational power. Again, color coding, linear or non-linear scales, goals, and statistical representations as described, supra, are optionally used in the presentation.

Figure 9:
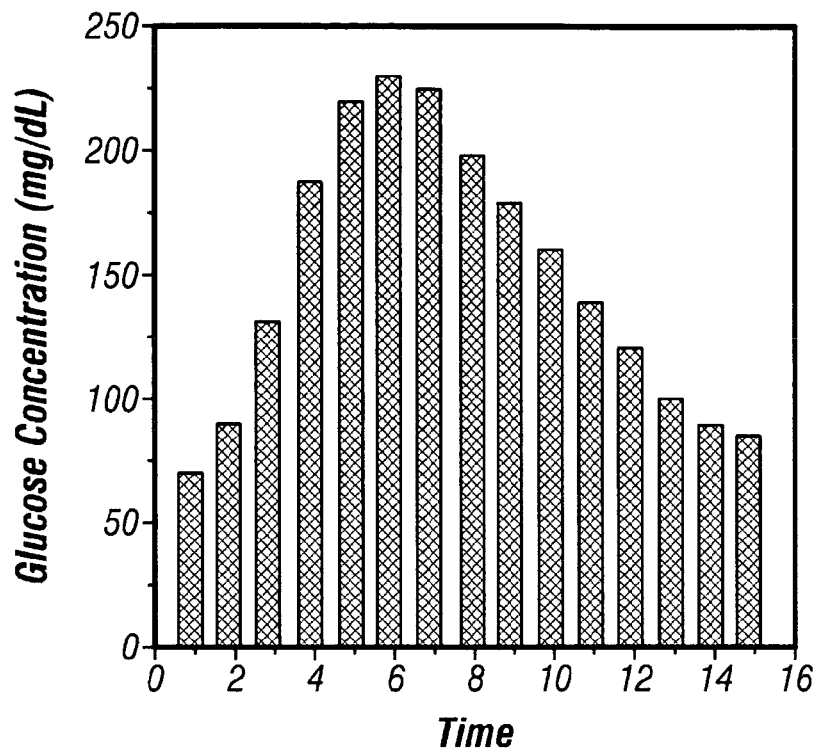
FIG. 9 presents a treadmill presentation of glucose concentrations according to the invention.

A fifth example uses a bar graph with multiple bars presented at a given time that move across the graph as a function of time. This is similar to a graphic on an exercise treadmill. This gives the user information on an extended history, information on the recent trends, and information allowing the projection of future glucose concentrations. An example is provided in FIG. 9. For example, FIG. 9 presents to the user in a rapid format that there glucose concentrations went up fairly rapidly to diabetic levels. This indicates to the user that for the state he was in when he ingested calories that should have been taken in fewer readily digested carbohydrate, should have been taken in the same amount of calories slower, should have been taken earlier or greater amounts of insulin, and/or should have been taken in a higher percentage of slower impacting calories, such as other sugars, protein or fat. Similarly, FIG. 9 shows the user that their glucose concentrations are decreasing, but not at an alarming rate. A steep decrease would alert the user of the possibility of dangerous upcoming low or hypoglycemic glucose concentrations. This graphical information is absorbed by the user to alter future activities, food intake, exercise, drug intake, or other events, as described below. In this embodiment, an overlay, such as a goal value, is indicated as a tick mark on the glucose axis or as a line or curve presented as an overlay.

Figure 10:
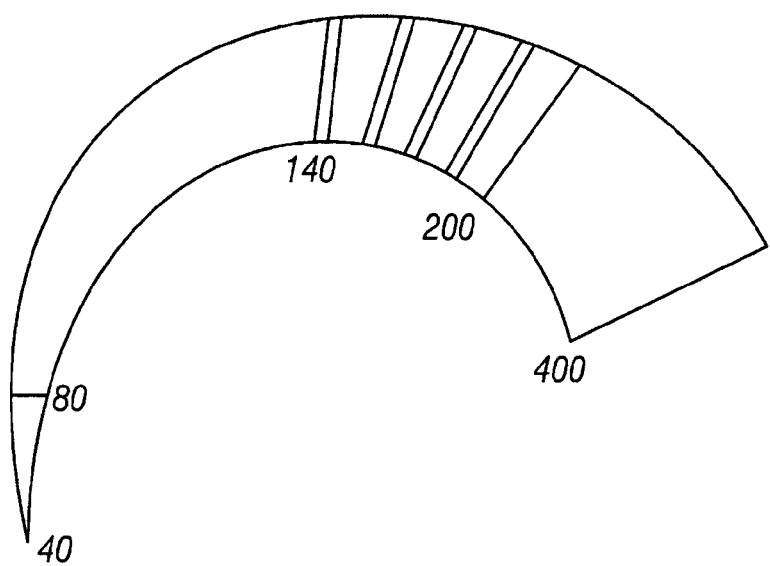
FIG. 10 presents a multidimensional presentation of a one-dimensional value according to the invention.

A sixth example shows the use of two or more dimensions to represent a one-dimensional vector of data. For example, glucose as a function of time is represented on a display, such as a tachometer. Referring now to FIG. 10, a tachometer is presented with several sections representing the continuum of low, normal, and high glucose concentrations. The sections are optionally color coded or graphically coded. For instance, the revved portion of the tachometer is a solid color, such as red and represents high sugar concentrations. Intermediate concentrations of sugar are represented as solid dashed bars. Normal physiological concentrations are represented by another color or open space, and hypoglycemic concentrations, low tachometer readings, are represented by another background. A needle, pointer, bar, or other graphical representation optionally represents the current, most recent, or historical glucose concentration or statistic.

Similarly, two-dimensional, three-dimensional, or four-dimensional representations are used to represent the underlying data. For example, volume bar graphs, a graphical symbol adjusted in size (two-dimensional or three-dimensional), or a geometric shape altered in size optionally represents the glucose concentration or mathematically transformed glucose concentration as a function of time. An extra, such as a fourth dimension, is optionally color or time.

In many of the examples, a number of time axes are appropriate. Examples of time axes comprise the last day, week, month, or n samples where n is an integer greater than or equal to two. Alternatively, the time axis represents sampling performed at other irregular or defined times. For example, the plots optionally represent data only on weekends, only on weekdays, or on holidays.

In all of the above example options, graphical representation optionally comprises color coding, linear or non-linear axis, goal concentrations, and/or historical concentrations, and/or statistical representations. As discussed, infra, these time-based events are optionally replayed in a compressed or mathematically transformed format to a viewer, such as the user or medical professional. The presentations optionally comprise any of variably scaled axis, color formatting, static images, and statistical representations of the data. As discussed, infra, individual glucose concentrations or clusters of glucose concentrations plotted against a given axis are optionally related to another cluster or event. In all cases, the intent is to provide information from the data to the viewer and/or human analyzer.

The foregoing six examples illustrate the extraction of information from tabulated data as a function of time. These types of plots aid in the reduction of data into information. These six examples are illustrative of the invention. Combinations and permutations of the examples are considered to be part of this invention.

Clustered Data

Another form of data presentation that conveys information from underlying data in a format that is more readily understood and used by an end user or a medical professional is clustering.

In the case of diabetes, one format for clustering the data is by a classification of the glucose concentration. For example, data are broken up or assigned into one or more of the following classes: hypoglycemic (hyperinsulinemia), normal, pre-diabetic (impaired), or diabetic.

Figure 11:
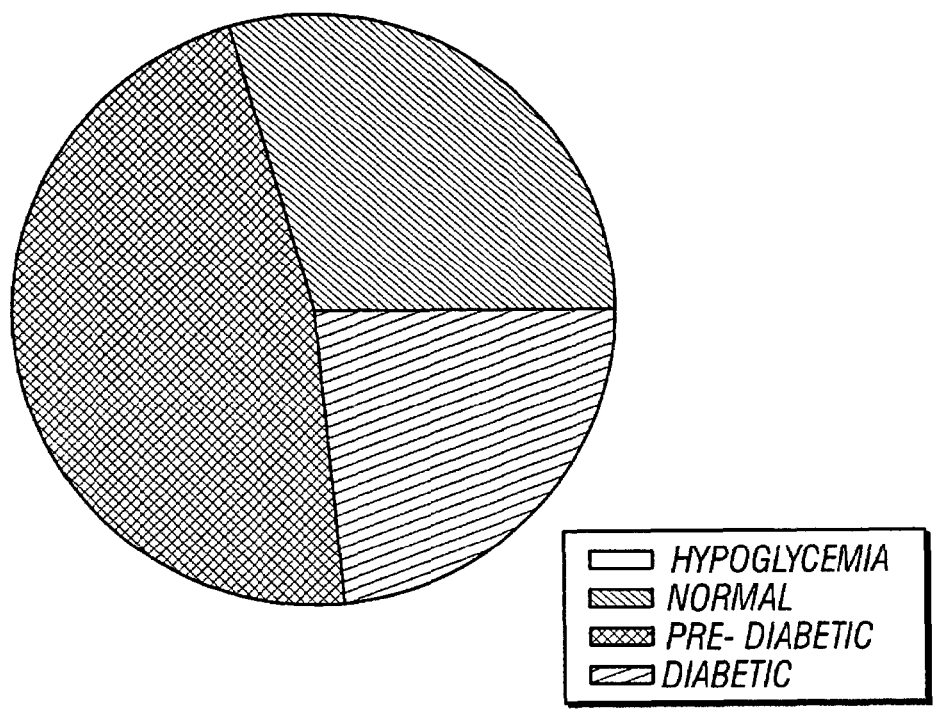
FIG. 11 presents a cluster analysis of glucose history versus defined groups according to the invention.

Referring now to FIG. 11, an example of clustering based upon glucose concentration ranges is presented. In FIG. 11, the data from the first subject of Table 1 is again used. The glucose concentrations are grouped into four groups: hypoglycemic, normal, pre-diabetic, and diabetic with ranges of 0 to 79, 80 to 120, 121 to 179, and 180 and higher, respectively. Any number of ranges are optionally used. For example, possible breakpoints between normal and pre-diabetes are 120, 126, and 140 mg/dL. Similarly, high ranges are defined as at or above 180, 200, 250, or 300 mg/dL.

With the original classification, FIG. 11 shows that for the data collected by this subject that this subject experienced no hypoglycemic episodes, was normal 29.4% or the time, had pre-diabetic readings 47% of the time, and experienced diabetic readings 23.5% of the time. This graph does not mean that the subject is 23% diabetic. Rather, it allows a diabetes educator or medical professional to observe the percentage of readings in which the subject is experiencing high glucose concentrations in a rapid format.

Selected data points or clusters of data points are then correlated with additional tabulated data to determine which actions the subject is performing that result in the selected readings. Once the actions are identified, the action is supported or taught against based upon the desirability of the resulting glucose concentrations. For example, a cluster of high glucose concentrations is selected, and found to correlate with the glucose determinations being made after supper. The professional then instructs the subject to future changes in treatments, such as reduced carbohydrates for dinner and/ or more insulin acting after dinner. The idea of clustering is to reduce a large number of readings into a reduced format for ease of immediate comprehension by both the professional and end-user. As glucose determinations are performed semi-continuously or continuously the graph optionally transposes into a percentage of time that the diabetic subject spends in each classification. One skilled in the art will immediately recognize that a large number of sub-classifications or other classifications are possible, such as 0 to 50 mg/dL, 51 to 100 mg/dL, 101 to 150 mg/dL, ..., 350 to 400 mg/dL. Groupings of data then are correlated to traditional long term markers, such as $HbA_1C$.

Another form of cluster presentation is the use of data presented on different axes at the same time. At its extreme, n glucose data points, where n is a positive integer, are represented as a single point on the plot. An example follows.

Figure 12:
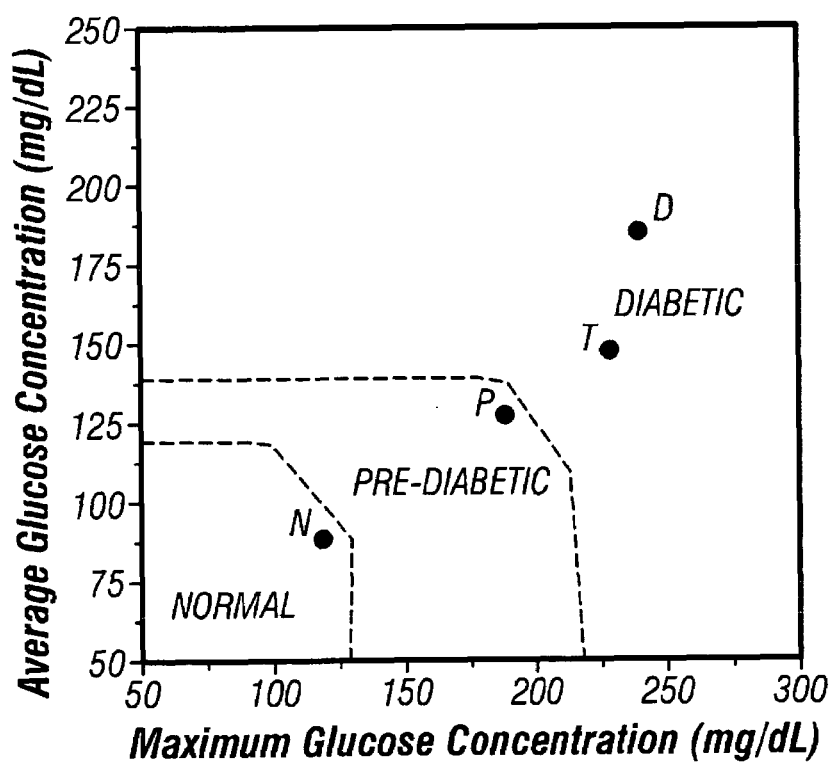
FIG. 12 presents a GTS treatment grid according to the invention.

A glucose tracking system treatment grid is presented as an example of reducing the total number of data points to a single datum. Referring now to FIG. 12, the average area, described infra, is presented versus the maximum glucose concentration. The average area is the average glucose concentration for n readings, where n is a positive integer. The n' readings are non-outlier readings for a defined period before or after an event, the readings for a given period, such as a day, or a subset of glucose readings in the analyzer memory. The average area is optionally normalized, baseline adjusted, offset corrected, and/or scaled. Similarly, the maximum glucose concentration on the x-axis is defined for a particular period. In this format, a non-diabetic individual has data points in the lower left hand corner where maximum and average glucose concentrations are low. For a diabetic individual, data points occur toward the right and up on the graph. Simply stated, the diabetic has higher peak glucose responses and typically stays higher for a longer period of time bringing up the average. Data points between these extremes result for borderline, impaired, or pre-diabetic individuals.

The glucose tracking system treatment grid is optionally broken into several regions. The regions suggest diabetic, pre-diabetic, and normal ranges. Another region is optionally added to the grid for hyperinsulinemia. These lines are artificial dividers for aiding in diagnosis and treatment of a continuum of possible states. The region dividing lines are suggestive of how to differentiate data. They act as guides to suggest how normal, pre-diabetic, or diabetic a given subject is or has been over the last n reduced data points. For a given individual, the last n events, such as a meal or a day, worth of data is represented by data points on the grid. Each point optionally represents a greater number of data points. This gives the user or medical professional a quick overview of the state of the individual. Some examples follow for clarity.

Figure 13:
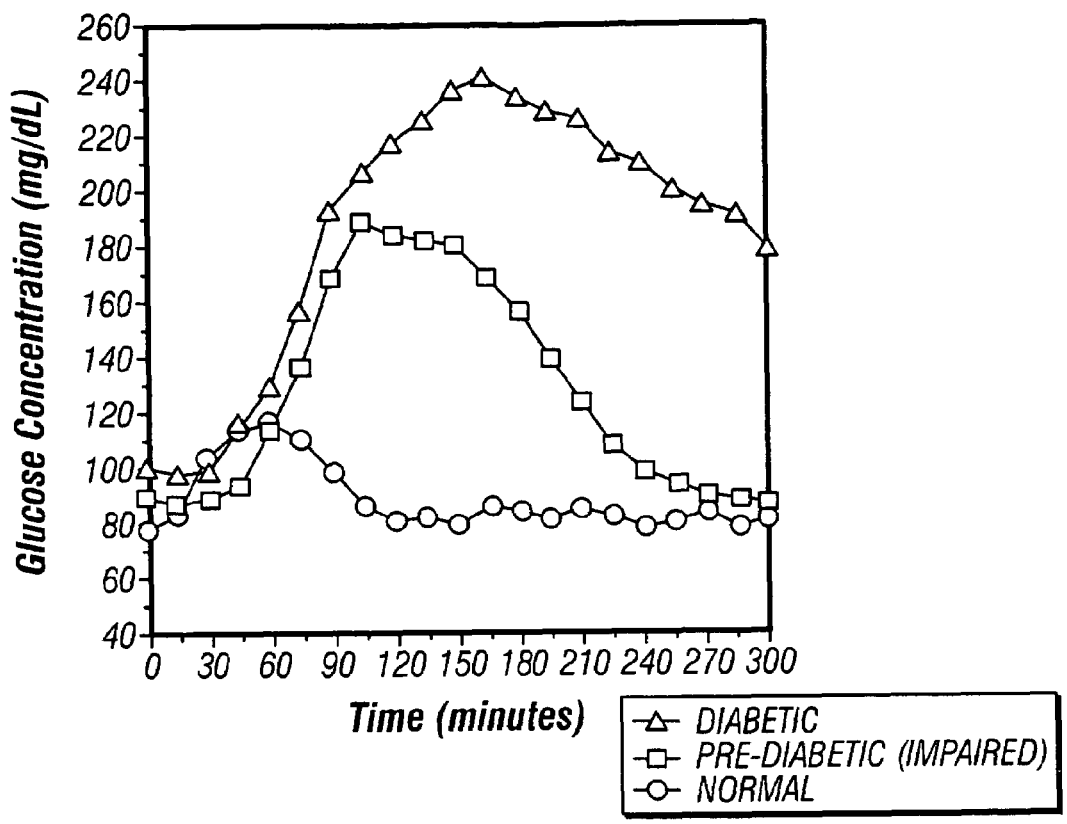
FIG. 13 presents typical glucose profiles.

In FIG. 12, the average glucose concentration since the last meal event is plotted against the maximum glucose concentration since the last meal event as an illustrative example on a glucose tracking system treatment grid. This plot reduces a large number of data points to information with a fewer number of data points. For example, the data presented in the treadmill presentation of FIG. 9 is represented as a single point. This point is labeled 'T' in FIG. 12. Three additional glucose profiles are presented in FIG. 13. These profiles represent typical normal, pre-diabetic, and diabetic glucose concentration profiles. These three glucose profiles are presented as 'N,' 'P,' and 'D' on FIG. 12, respectively. Thus, it is observed in FIG. 12 that the four glucose profiles are each represented by a single point on the GTS grid. It is rapidly observed that the treadmill subject has diabetic tendencies, as does the subject with the diabetic glucose profile shown in FIG. 13. Similarly, the pre-diabetic subject with the glucose profile in FIG. 13 shows a result in the pre-diabetic range of FIG. 10 and the normal subject glucose profile of FIG. 13 is represented as a single data point in the normal region of FIG. 12.

Figure 14:
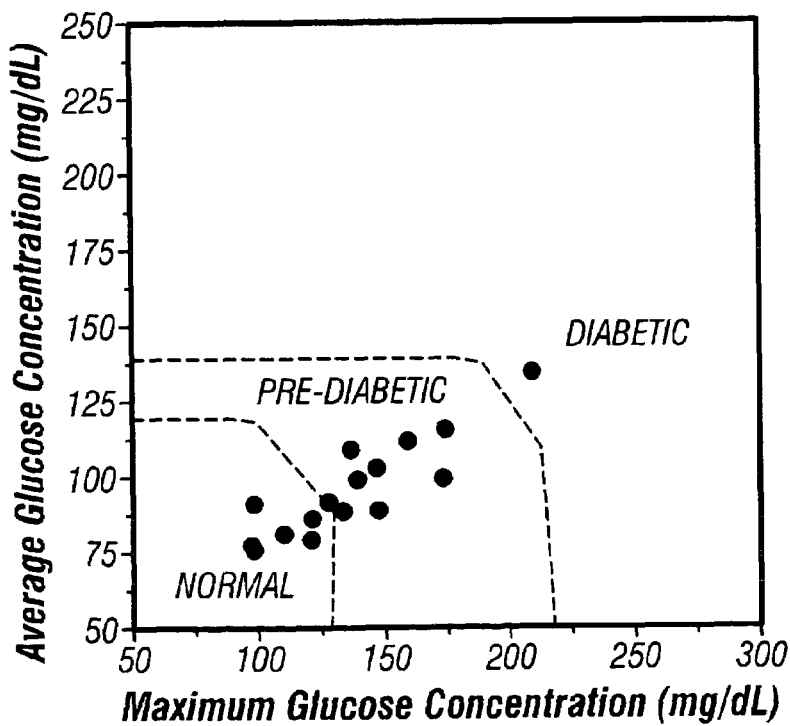
FIG. 14 presents a GTS diagnosis grid according to the invention.

Referring now to FIG. 14, another illustrative example is provided. This subject has fifteen glucose profiles reduced to 15 data points. The data show that the individual is experiencing glucose profiles that are not normal, but would not be classified as diabetic. Roughly half of the points fall into the pre-diabetic region. However, the individual has habits or tendencies that drive him into a diabetic profile. This could be, for example, the ingestion of a large amount of carbohydrate rich food at one time. The important point is that this individual may not be classified as a diabetic based upon a fasting glucose concentration, a $HbA_1C$ level, by symptoms, or through a glucose tolerance test. Yet the individual has diabetic tendencies and is a strong candidate for developing diabetes. This is recognized immediately from this plot. Thus, this or related plots are used to diagnose diabetes, pre-diabetes, diabetes tendencies, or hyperinsulinemia. Further, if data points are associated with events, such as a given meal type, insulin therapy, or drug therapy, such as the use of glucophage, then the representation of the data is used to adjust a treatment. Unlike Hemoglobin A1C levels that average responses over a period of months, the treatment is adjusted to an event.

These plots give an individual the ability to determine for themselves rapidly how their actions translate into glucose responses of different risk levels. For example, an individual eats a lunch rich in carbohydrates and determines after several such events that they maintain normal glucose concentrations. Similarly, another individual may determine that the same meal results in unhealthy concentrations of glucose. This individual determines that they can eat a smaller portion with acceptable resulting glucose concentrations, or they may determine that another meal type is more appropriate for themselves based upon their resulting glucose profiles. An important aspect of the presentation is allowing the user to determine rapidly in a graphical or reduced data format their response to a given action. Naturally, this self-adjustment and self-treatment is best used in combination with the guidance of medical professionals. However, the reduction of abstract glucose concentrations and profiles into interpretable data allows a user rapid feedback on the effect of their habits. This is particularly useful because people are creatures of habit.

The example in FIG. 12 used average area versus the maximum glucose concentration. A large number of alternative axes could be used. For example, the total area is used in place of average area. Normalization of axes, scaling, linear and nonlinear transformations, and mapping to alternative scales, such as to HbA1C level are optionally used. The key is the reduction of the glucose concentration data points into a graphical or new scalar representation of their glucose history or profile into a discrete and readily interpretable representation.

Audio/Tactile

Glucose concentrations or information derived from multiple glucose concentrations have heretofore been presented through visual means, such as in Arabic numeral, graphical, or video format. Representation of analyte concentrations are also possible through other senses, such as through an audio or tactile output. Audio or tactile output is advantageous in a number of situations. For example, many diabetics are sight impaired making visual representation of data difficult. As a second example, some individuals learn better through audio cues compared to visual cues. In yet another example, many individuals assimilate information most readily when input is provided through more than one sensor, such as visual, audio, or tactile. In still yet another embodiment, glucose values are output from a noninvasive analyzer to the user through a tactile output, such as Braille.

Audible output of analyte concentrations is described in a variety of formats, herein. For example, when a glucose concentration is observed to be falling at a rate that in light of the current glucose concentrations predicts a future or imminent hypoglycemic event, the user is warned by a buzzer, alarm, voice synthesized audible projection, or a vibration of the device. Similar warnings or informative events are used when glucose concentrations are going too high or when a target value or range is obtained or lost.

An optional audible output is an earcon. An earcon is an abstract or synthetic tone structured to convey information through a link learned by the listener. Earcons are constructed from simple building blocks called motives. These are short, rhythmic sequences of pitches that are optionally combined in different ways. A motive is a brief succession of pitches arranged in such a way as to produce a tonal pattern sufficiently distinct to allow it to function as an individual recognizable entity. See J. Ballas, J. Howard, *Interpreting the language of environmental sounds* Envirionment and Behaviour, vol. 19(1), pp. 91-114 (1987). For example, an earcon provides an interface between an analyzer and a user. The user learns their glucose concentration through the earcon. For instance, an earcon output optionally provides the user an audible signal of their analyte concentration, such as a noninvasively determined hyperglycemic glucose concentration that is audibly output to the user. Examples of audible output include one or more tones, motives, or rhythms that are of varying pitch, timbre, register, and/or dynamic. For instance, an earcon outputs an audible signal to the user, such as a motive, rhythm, pitch, timbre, register, or dynamic. These musical terms are well known in the musical arts and are briefly reviewed here. A motive is a brief succession of pitches. A rhythm is a periodic repetition with a reoccurring of emphasis. A pitch is a tone, such as one of ninety-six notes used in Western music. Timbre is the duration of a tone. Register is position on a musical scale. For example, high register corresponds to high pitches and low register to a low note. A dynamic is the volume of a motive.

Function or Event

Glucose concentration profiles or responses as a function of time are discussed throughout this specification. In addition, glucose concentration profiles or responses tied to one or more event are generated, analyzed, and used. Generally, these events include such actions as a food or liquid intake, exercise, or the ingestion or injection of a drug. In its broadest sense, glucose data are correlated to an event or to time after an event. Several examples follow.

EXAMPLES

An individual wishes to understand how they respond in terms of glucose concentration to an intake of calories. The analyzer records, based upon user intake, parameters, such as calories, carbohydrates, fats, and proteins along with the time they were ingested. Alternatively, foods are input into the analyzer and a lookup table is used to convert the foodstuffs into the above listed parameters e.g. carbohydrates, fats, and proteins. For example, the user inputs that he ate an apple at a given time and the lookup table is used to input the number of carbohydrates ingested at that time. Alternatively, preprogrammed meals or meal types are incorporated into the system. The user then selects the meal type and a conversion to the above listed parameters is automatically performed. Responses to these parameters are then made based upon subsequent glucose concentration responses. Responses of an individual in terms of glucose concentration are generated based upon ingested carbohydrates of varying forms, proteins, and fats each of varying levels of detail and forms. These responses are output in any of the forms presented herein, such as the glucose treatment system grid. For example, a query of all meals containing less than 80 grams of carbohydrates results in a given set of data on a glucose treatment system grid. Alternative grids are generated for all combinations of sugars, fats, and proteins.

Estimating Future Glucose Concentration

Based upon entered values or upon a calibration routine, predictions are generated that output the expected glucose profile for a given food intake. Calibrations are generated with fixed amounts or combinations of sugar, fat, and protein intakes. Thus, a user inputs a meal that they are about to take, and an expected glucose concentration is generated. This is the basis of a glucose management system (GMS). Additional parameters for a GMS include insulin or other glucose management drugs, such as glucophage, time of day, type of diabetes, age, sex, weight, height, exercise, and body mass index (BMI).

Combination of Graphical Representations

Combinations of graphical presentation types presented herein are optionally used in conjunction. For example, the software is configured such that a second graphical display type is used to represent a given section of a first graphical display type. For example, this subject finds that 100% of their normal readings occur before noon and that the majority of their diabetic readings occur after five p.m. This is shown with a time analysis of a given pie section.

General to Many Embodiments

One aspect of the invention is to reduce the number of pieces of data into manageable information. A second aspect of the invention is to provide the user or a medical professional information about his disease to aid in management and treatment of the disease. A third aspect of the invention is to allow the user to estimate future glucose concentration response profiles to an event, such as exercise, food intake, or intake of drugs used to treat diabetes.

In many embodiments of this invention, the reduced data display is presented with color coding, on linear or nonlinear scales, and with statistical reduction.

Hardware memory capabilities of the analyzer that hold glucose concentration as a function of time preferably allow graphical presentations, such as the sliding bar graphs of the third time example, updating bar graph similar to the fourth time example, the treadmill presentations of the fifth time example, and tachometer presentations similar to the sixth time. Optionally any of these presentation types are replayed on an altered time axis in a video-like format. For example, the medical professional or user plays all glucose concentrations collected in the last number of hours, days, weeks, or months in a condensed format presented in seconds or minutes. The display of the data is the original data played back faster or a reduction or chemometrics treatment of the data. For example, a moving average is presented as a function of time. A major attribute of this type of presentation is the quick conveyance of information to the viewer of a large amount of data. Each of the presentation types optionally have subsections or markers that indicate statistical representations of the data, such as a high glucose concentration, a low glucose concentration, or an inter-quartile range that remains visually displayed to the viewer. From this disclosure, additional statistical presentations will be obvious to those skilled in the art. Alternatively, one or more subsets of the stored data are presented. For example, glucose concentrations for a given time period of a day are presented. Similarly, glucose concentrations are presented that precede or follow an event, described supra. For example, concentrations from one to two hours after a meal of a given or any type are presented. Again the subsets may present all of the data, a subset of data, or transformations of the data. Similarly, video representation of clusters is presented.

Some examples of the usefulness of a video presentation follow. The viewer optionally sees glucose concentrations that go up and down rapidly and/or often and recognizes that their glucose concentrations are not well controlled. The viewer optionally sees a large percentage, majority, or plurality of data that are color coded to normal values and recognizes or is informed of their level of control to normal concentrations. This is alternatively used to recognize visually how often they are mildly elevated as for example a number from 140 to 200 mg/dL or highly elevated, such as for example 300 to 500 mg/dL. Graphical representations of statistical concentrations, such as high and low values, optionally remain on screen after the condensed concentrations have been presented in video format to allow rapid analysis of the extreme concentrations. Hypoglycemic concentrations optionally appear in a warning color or have associated with them an audio cue, signal, or voice synthesized message. The presentations are optionally overlaid onto images representative of target ranges. For example, if a user has a target glucose value of 150 mg/dL or less then a line or representation of this target is displayed along with the video presentation giving immediate feedback to the viewer.

A number of spectrometer configurations are possible for this measurement as are outlined, supra. At a minimum, the analyzer includes a source of near-infrared radiation, a wavelength selection system, an interface to the patient, photon guiding optics, a detector, data processing means, and output means. Permutations and combinations of the embodiments described herein are also envisioned.

In the foregoing discussion, the preferred embodiments of the invention have been described with respect to determination of a glucose concentration. Additional analytes for concentration or threshold determination are those found in the body including but not limited to water, protein, fat and/or lipids, cholesterol in its various forms, blood urea nitrogen (BUN), both therapeutic and illicit drugs, and alcohol.

Those skilled in the art will recognize that the present invention may be manifested in a variety of forms other than the specific embodiments described and contemplated herein. Departures in form and detail may be made without departing from the spirit and scope of the present invention. Accordingly, the invention should only be limited by the Claims included below.

The invention claimed is:

1. An apparatus for analyte concentration display, comprising:
   a near-infrared noninvasive glucose concentration analyzer;
   a display module integrated into said analyzer; and
      means for video graphic display of historical analyte concentrations in a time compressed format on said display module.

2. The apparatus of claim 1, wherein said historical analyte concentrations represent at least five glucose concentrations.

3. The apparatus of claim 2, said historical analyte concentrations further comprising a time period, wherein said video graphic display represents glucose concentrations within said time period.

4. The apparatus of claim 3, wherein said time period comprises a period of any of about:
   a period of a glucose excursion;
   a day;
   a week;
   a month; and
   several months.

5. The apparatus of claim 4, wherein said video graphic display comprises any of:
   a slider graph;
   a treadmill graph; and
   a tachometer graph.

6. The apparatus of claim 5, wherein said video graphic display comprises a first animated graphical representation of at least one of said historical glucose concentrations.

7. The apparatus of claim 6, wherein said first animated graphical representation represents any of:
   a current time stamped glucose concentration; and
   an individual glucose concentration, wherein said individual glucose concentration comprises one of said historical analyte concentrations.

8. The apparatus of claim 7, wherein said video graphic display comprises a second animated graphical representation of any of:
   a maximum achieved glucose concentration;
   a minimum achieved glucose concentration;
   a targeted glucose concentration;
   a targeted maximum glucose concentration; and
   a targeted minimum glucose concentration.

9. The apparatus of claim 3, further comprising a user interface.

10. The apparatus of claim 9, wherein said time period is controlled through said user interface.

11. The apparatus of claim 1, wherein said display module comprises a color display screen.

12. The apparatus of claim 11, said historical analyte concentrations further comprising at least three physiological glucose concentration ranges, wherein said video graphic display represents said historical glucose concentrations for each of said ranges in different colors.

13. The apparatus of claim 12, wherein said physiological glucose concentration ranges comprise at least two of:
   a range of hyperglycemic glucose concentrations;
   a range of normal glucose concentrations;
   a range of hypoglycemic glucose concentrations; and
   a targeted glucose concentration range.

14. The apparatus of claim 11, wherein said display module comprises an input touch screen.

15. The apparatus of claim 1, wherein said analyzer comprises:
   a base module in a first container;
   a communication bundle having a first end and a second end, wherein said first end connects to said base module; and
   a sample module in a second container separated from said first container, wherein said second end of said communication bundle connects to said sample module.

16. An apparatus for representation of data associated with historical noninvasive glucose concentrations, comprising:
   a near-infrared based noninvasive glucose analyzer;
      means for conveying underlying information of tabulated data via a user interface module, wherein said means for conveying comprises:

means for reducing said tabulated data via clustering into groups;

means for generating a correlation between at least one of said group to a user performing action; and means for presenting graphically to the user said correlation, wherein presentation of said correlation of said action to said group provides said underlying information to the user or a medical professional allowing action specific diagnosis or treatment.

17. The apparatus of claim 16, wherein said analyzer comprises of:

a sample module in a first housing;

a base module in a second housing; and means for communication between said sample module and said base module.

18. The apparatus of claim 16, wherein a group of said groups comprises:

a set of said glucose concentrations defined by class.

19. The apparatus of claim 16, wherein said step of reducing said tabulated data via clustering into groups result in any of:

a group of points representing said glucose concentrations represented on two or more axes; and a group of points relative to a threshold.

20. The apparatus of claim 19, wherein said axes comprise any of linear, nonlinear, average, maximum, and area representations.

21. The apparatus of claim 16, further comprising means for selection of a cluster via the user interface module.

22. The apparatus of claim 21, wherein said user interface module comprises any of:

a touch screen;

a stylus;

a keyboard; and a button driven interface, whereby selection of at least one of said historical glucose concentrations is performed.

23. The apparatus of claim 22, wherein said means for selection of a cluster comprises any of:

a look-up table; and a historical table.

24. The apparatus of claim 23, wherein said means for selection of a cluster further comprises any of:

a central processing unit; and a programmable logic device.

25. The apparatus of claim 16, wherein said the means for presenting graphically comprises publication on the user interface module of any of:

a pie graph;

a histogram;

a time of day analysis;

a glucose treatment grid; and a tabulation of said values of variables associated with points in said cluster.

* * * * *